United States Patent [19]

Masilamani et al.

[11] 4,227,028

[45] Oct. 7, 1980

[54] REGIOSELECTIVE SUBSTITUTION AT CARBON ATOM VINICAL TO DOUBLY BONDED TERTIARY CARBON ATOM BY SULFUR DIOXIDE CATALYSTS

[75] Inventors: Divakaran Masilamani, Morristown; Milorad M. Rogic, Whippany, both of N.J.

[73] Assignee: Allied Chemical Corporation, Morris Township, Morris County, N.J.

[21] Appl. No.: 16,578

[22] Filed: Mar. 1, 1979

Related U.S. Application Data

[62] Division of Ser. No. 862,313, Dec. 20, 1977.

[51] Int. Cl.² .......................... C07C 13/18; C07C 5/22
[52] U.S. Cl. .................................. 585/941; 585/350; 585/377; 585/377
[58] Field of Search ................ 585/350, 377, 378, 941

[56] References Cited

U.S. PATENT DOCUMENTS

| | | | |
|---|---|---|---|
| 3,475,507 | 10/1969 | Sedlak | 585/941 |
| 3,849,458 | 11/1974 | Dinh-Nguyeu et al. | 585/941 |

FOREIGN PATENT DOCUMENTS 532685 1/1941 United Kingdom .

OTHER PUBLICATIONS

DeBoer et al. Kon. Ned. Acad. W. Proc. 50, 1181–1188, 1947.
Keuzenkamp et al. J. Amer. Oil Chemists Soc. 479–481, 1949.
Waterman et al., Research Suppl. 583–585, 1949.
Vohwinkel, Farbe U. Lack 65, 571–573, 1959.

*Primary Examiner*—Veronica O'Keefe
*Attorney, Agent, or Firm*—Robert A. Harman

[57] ABSTRACT

A process for regioselective isomerization of organic compounds having a carbon-carbon double bond at a tertiary carbon atom by sulfur dioxide induced allylic rearrangement of a hydrogen atom and/or replacement of a proton in the allylic position by a deuteron. The organic compound is contacted with sulfur dioxide at temperatures between about 0° and 70° C. for a time sufficient to effect such isomerization to a more stable isomer; and if deuteration is to take place $D_2O$ is provided in the solution.

5 Claims, No Drawings

REGIOSELECTIVE SUBSTITUTION AT CARBON ATOM VINICAL TO DOUBLY BONDED TERTIARY CARBON ATOM BY SULFUR DIOXIDE CATALYSTS

This is a division of application Ser. No. 862,313, filed Dec. 20, 1977.

FIELD OF THE INVENTION

This invention relates to a process catalyzed by sulfur dioxide for regioselective isomerization of olefins having a proton (i.e. a hydrogen nucleus) or isotope thereof located on a carbon atom vicinal to a tertiary double bonded carbon atom by allylic rearrangement of a hydrogen atom; or selective hydrogen deuterium exchange in the allylic position of such a double bond.

BACKGROUND OF THE INVENTION

The isomerization of organic compounds having double bonds has been of interest to chemists and there are many methods available such as the isomerization in the presence of acids providing protons like sulfuric acid. However, isomerizations involving acids like sulfuric acid are not specific and is hard to predict where the double bond will end up and what kind of an equilibrium mixture of all the possible isomers will be obtained.

Replacing specific C-H bonds with C-D bonds has enabled chemists to understand reaction mechanism by measuring primary and secondary kinetic isotope effects. Biologists and biochemists have used deuteration techniques to follow the fate of specific hydrogens on a molecule in biological processes. Most deuteration procedures are involved and expensive. A simple procedure for regioselective deuterium using a cheap deuterism source such as $D_2O$ is attractive. Olefins are important starting compounds for organic synthesis. A procedure for regioselective deuteration of olefins with $D_2O$ is very desirable for producing deuterated compounds.

Sulfur dioxide has been employed for the isomerization of olefins and this has been disclosed in a British patent to Colgate-Palmolive Peet Company No. 532,685 accepted on Jan. 29, 1941. In particular, this patent is concerned with the alkylation of aromatic rings by reaction with alkyl halides or olefins and the acylation of aromatic compounds by reaction with carboxylic acid halides or carboxylic acids and with the polymerization, isomerization and condensation and cyclization of hydrocarbons and their derivatives. Including saturated and unsaturated aliphatic cyclic, alicyclic aromatic and substituted aromatic hydrocarbons and many of their derivatives. The isomerization of normal pentene gives isoamylene and amylene and 3 methyl-butene-1.

J. H. Deboer in *Koninklijke Nederlandse Academie Wetenschappen Proc.* Vol. 50, page 1181 [1947] discloses a mechanism of isomerizations of unsaturated fatty acids by $SO_2$. This application is mostly concerned with cis-trans isomerization and catalyzed conjugation. However, it does not relate to isomerization of double bonds at tertiary carbon atoms.

A. Keuzenkamp in the *Journal of the American Oil Chemists Society*, page 479, issued September, 1949, describes the catalytic isomerization of cod liver oil with sulfur dioxide. The disclosure does not relate to isomerization at tertiary carbon atoms.

H. I. Waterman in *Research Supplement* 2-12, page 583, issued 1949, describes the isomerization of olefinic double bonds by sulfur dioxide. This application describes the shifting of double bonds in the presence of sulfur dioxide but does not mention isomerization involving tertiary carbon atoms.

F. Vohwinkel in *Farbe und Lack*, Vol. 65, page 571 [1959] reviews the effect of sulfur dioxide on vegetable oils, for catalyzing the shifting of isolated double bonds to conjugated double bonds, the cis-trans isomerization and the polymerization. He does not mention any effects relating to the isomerization involving tertiary carbon atoms.

Walter E. Rathjen et al. in U.S. Pat. No. 3,278,567 discloses a process for conjugating and isomerizing drying oils and products with sulfur dioxide at temperatures between 475° F. and below 550° F. He finds that cis-trans isomerization occurs for the drying oils but does not report any effects on tertiary olefinic carbon atoms.

A. W. Hudgell et al. in *J. Chem. Soc.* 1954, 814–16 disclose the isomerization of diene and triene steroids in sulfur dioxide to identified and unidentified products at reaction temperatures between 20° C. and predominantly 100° C. It was believed that the isomerizations are initiated by protons produced by the water-sulfur dioxide system. None of the methods mentioned are specific for obtaining a regioselective isomers from a particular class of olefins and they do not involve particular tertiary carbon atoms.

SUMMARY OF THE INVENTION

It is an object of the invention to provide a method for selective isomerization by allylic rearrangement of a hydrogen in olefins having double bonded tertiary carbon atoms. It is a further object of the invention to provide such isomerization of such carbon-carbon double bonds at tertiary carbon atoms which is specific and results in essentially a single product from a given olefin, and not a mixture. It is another object of the invention to provide a means of hydrogen-deuterium exchange in the allylic position referring to such double bond without further disturbing other parts of an organic molecule.

It is another object of this invention to provide a method for regioselective deuteration of the above-mentioned category of olefins using deuterium oxide as the selective inexpensive deuterium source.

This invention provides a method for allylic rearrangement wherein a hydrogen nucleus or isotope thereof in an olefinic compound having a tertiary double bonded carbon atom is transferred from a carbon atom, vicinal (i.e. directly linked) to the tertiary double bonded carbon atom to the non-tertiary double bonded carbon atom accompanied by shifting of the double bond; and/or replacement of such first nucleus by isotope exchange at the allylic position in such compound, by an isotope nucleus. To effect the allylic rearrangement a solution is formed of the olefinic compound in liquid sulfur dioxide, whereupon the said nucleus is removed from said vicinal carbon atom as a result of the formation of a complex with the sulfur dioxide. This nucleus migrates by allylic rearrangement to said non-tertiary double bonded carbon atom, with shifting of the double bond. In the isotope exchange, the site left unoccupied by the removal of such nucleus is filled by an isotopic nucleus supplied by the same compound from a different site thereof or by another compound such as $D_2O$ present in the sulfur dioxide solution, whereby exchange of the two isotopic nuclei occurs.

The extent of deuteration is limited only by the amount of deuterium oxide used for deuteration. During deuteration, the olefins are not isomerized.

DETAILED DESCRIPTION OF THE INVENTION

Compounds useful in the present invention include those having the formula

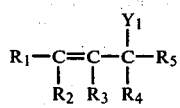

wherein $Y_1$ is hydrogen, deuterium or tritium; wherein $R_1$, $R_2$, $R_4$, $R_5$ are hydrogen, deuterium, tritium, or an organic group having a carbon atom bonded to the allylic group such as alkyl, aryl, arylalkyl, alkylaryl, cycloalkyl, haloalkyl, haloaryl, substituted alkyl, substituted aryl and wherein $R_3$ is an organic group having a carbon atom bonded to the center of the allylic group such as alkyl, aryl, arylalkyl, alkylaryl, cycloalkyl haloalkyl, haloaryl, substituted alkyl, substituted aryl. The substituents on the carbon atom next nearest to the allylic group include nitro, methoxy, alkoxy, mercapto, amino, primary amino, secondary amino, heterocyclic groups, and the like.

Compounds useful as starting materials for the isomerization of the present invention include:
(+) or (−) or (±) -beta-pinene
methylene cyclohexane
2-methyl pentene-1
3-methyl pentene-2
2,3-diphenyl-1-propene
2-methyl butene-1
2-chloromethyl-butene-1
2-methyl butene-2
2-methyl pentene-2
2-ethyl butene-1
2,3-dimethyl butene-1
2,3-dimethyl butene-2
2-methyl hexene-2
3-methyl hexene-2
2-ethyl pentene-1
2,4,4-trialkyl-pentene-1 and -2
methylene cyclopropane
methylene cyclobutane
isopropylidine cyclopentane
1-alkyl cyclohexene
ethylidene cyclohexane
propylidene cyclohexane
1 methyl-3-isopropylidene cyclohexane
1 methyl-4 isopropylidene cyclohexane
1-methyl cyclopropene-1
1 methyl cyclohexene
1 methyl-4-isopropylcyclohexene-1
1 methyl-4-isopropylcyclohexene-3
1 methyl cyclopentene
d-limonene
terpinolene
(3-butenyl)-cyclohexene-1
1 methyl-2-(3 butenyl)-cyclohexene-1
alpha-terpinene
gamma-terpinene
1-alpha-phelladrene
d-alpha-phelladrene
1-phenyl-propene-1
1-(p-tolyl)-propene-1
1-(p-chlorophenyl)-propene-1
1 phenyl-3-methyl butene-2
1,1,3-triphenyl propene-1
1,2,3,3-tetraphenyl propene-1
1,3-diphenyl butene-1
2,3-diphenyl butene-2
2,4-diphenyl-4-methyl pentene-2
1-methyl-2-(-1-naphtyl-ethyl)cyclopentene-1
1-methyl-2-benzyl-4-isopropyl cyclohexene-1
1-methyl-2-(1′-naphtyl)-cyclohexene-1
1-methyl-2-(-3′-acenaphthylethyl)-cyclohexene-1 and
1-methyl-2-(-9′-phenanthryl ethyl)-cyclohexene-1.

References to a number of these compounds can be found in Gustav Egloff et al: *Isomerization of Pure Hydrocarbons,* Reinhold Publishing Co., New York (1942).

The tertiary carbon atom can be linked by a double bond to methylene, ethylidene, propylidene, butylidene, pentylidene, isopropylidene, isobutylidene, cyclohexylidene, cyclopentylidene, benzylidene, alkylidene, cycloalkylidene, arylalkylidene. The tertiary carbon atom can be linked by single bonds to methyl, ethyl, propyl, isopropyl, butyl, isobutyl, pentyl, isopentyl, hexyl, heptyl, octyl, nonyl, decyl, cyclobutyl, cyclopentyl, cyclohexyl, cycloheptyl, benzyl, vinyl, alkyl, alkylene arylalkyl groups provided one of the ligands of one of the carbon atoms next to the tertiary carbon atom is a singly charged nucleus such as hydrogen.

The alkyl and alkenyl groups connected to the tertiary carbon atom may be substituted or linked by halogens, nitro, sulfonic acid, amino, hydroxy, alkoxy, ester, carboxyl, keto and aldehyde groups.

Since free energy differences between the 1,1-disubstituted, trisubstituted and tetrasubstituted olefins are substantial (often above 2 kcal/mol) percentage conversion of one olefin to another is high (of the order of 90% or above) and the recovery of the olefin after isomerization is quantitative.

In a typical operation the olefin to be isomerized is taken in a previously dried pressure vessel which is provided with stirrer and a cooling system and supply means for $SO_2$ gas. The amount of olefin is not critical. It can be in the range of between about 0.03 mol to commercial quantities. The pressure vessel can be of various sizes with 100 mililiter convenient in the isomerization of small quantities of olefins (0.03 to 0.05 mol). For larger quantities appropriately sized vessels are employed. The sulfur dioxide gas is taken from a source such as a commercial cylinder and is then dried by passing it through a molecular sieve. Then the $SO_2$ is condensed into the pressure bottle by the temperature gradient generated by the dry ice acetone mixture. After the sulfur dioxide has been collected the source bottle is closed by means of a sample collecting setup. Then the pressure vessel is closed and warmed up to room temperature and the contents can be stirred magnetically until isomerization is complete. Under these conditions the internal pressure ranges from about 35 to about 50 pounds per square inch. After the complete reaction, sulfur dioxide is allowed to escape. The escape can be performed by employing sulfur dioxide excape nozzle which collects the evolving sulfur dioxide into a 50% sodium hydroxide solution or, if desired, the sulfur dioxide can be recycled. After the $SO_2$ has been removed the isomerized olefin is directly distilled or it may be extracted with 50 ml of methylene chloride and the resulting solution is dried for instance, with sodium sulfate, filtered and concentrated. The crude isomerized olefin can be distilled if necessary. Usually the yields are quantitative. When highly volatile olefins are isomerized, for instance pentenes, then the escaping sulfur dioxide gas removes most of the olefins. In such a situation, the escaping olefins can be trapped in a layer of ether placed above the 50% sodium hydroxide solution.

pressed and hence isomerization does not occur. However, the sulfinic acid group exchanges its hydrogen for deuterium from deuterium oxide in a fast reaction before it reverses back to form starting olefin and sulfur dioxide. The starting olefin gets deuterated in the reverse reaction.

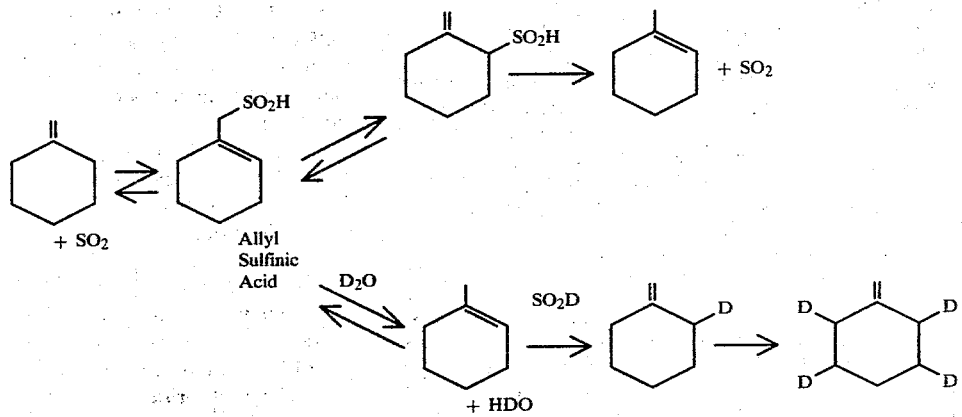

Isomerizations can be carried out at temperatures above room temperature and in this case stainless steel bombs are advantageously employed instead of a pressure bottle. Otherwise the set up and working procedures are identical. The sulfur dioxide employed in the reaction can be diluted with a suitable organic solvent soluble in $SO_2$ such as methylene chloride or other chlorinated hydrocarbons. The isomerization can also be performed when the catalyst sulfur dioxide is absorbed to a solid medium such as an alumina suitable for column chromatography.

For the deuteration of olefins with deuterium oxide in liquid sulfur dioxide a procedure identical to the isomerization method described and disclosed above is employed. Both the olefin and the deuterium oxide are placed in the pressure bottle or autoclave. Sulfur dioxide is then condensed. Deuterium oxide forms a separate phase above the liquid sulfur dioxide. The contents must be stirred and agitated for effective deuterization of the olefin. The isolation of the products is very similar to the isolation in the case of the isomerization. However, after removing the sulfur dioxide 50 ml of methylene chloride is added, and the deuterium oxide/water layer is removed before drying the methylene chloride layer. The deuterization procedure at temperatures higher than room temperature are carried out in stainless steel bombs of suitable capacity.

Regioselective isomerization and deuteration of 1,1-disubstituted, trisubstituted and tetrasubstituted olefins in liquid sulfur dioxide is explained by the "ene" reaction of sulfur dioxide with the above olefins to form allylsulfinic acids which are short-lived high energy intermediates. After addition of sulfur dioxide to the double bond for forming a 1,3 dipolar intermediate, deprotonation of an allylic hydrocarbon forms allylsulfinic acid, succeeded by 1,3 rearrangement of the allylsulfinic acids to form rearrange allylsulfinic acid which protonates the double bond giving rise to a second 1,3 dipolar intermediate which then ejects sulfur dioxide to form the isomerized olefin. In the absence of water or $D_2O$, the sulfinic acid group undergoes an allylic rearrangement followed by retro-ene reaction to form the isomerized olefin and sulfur dioxide. In the presence of deuterium oxide, the allylic rearrangement is sup- The rate of isomerization is first order in olefin and first order in sulfur dioxide and varies from olefin to olefin. In general, monocyclic and alicyclic olefins isomerize fast (half-life few seconds to 12 hours for 1 molar solutions of olefin in liquid sulfur dioxide at room temperature). Bicyclic olefins with allylic hydrogens twisted out of the plane of the carbon-carbon double bond isomerize slowly (half-life of the order of weeks). Isomerization rates are increased (1) by increasing the concentration of sulfur dioxide, (2) by raising the temperature and (3) by using neutral alumina as catalyst.

The rate of deuteration of olefins depends also on the olefin. Unstable olefins which easily form allyl sulfinic acids are deuterated fast. The extent of deuteration is limited only by the availability of deuterium from $D_2O$. By taking a large amount of $D_2O$, deuteration to an extent of 95% of the regiospecific allylic hydrogens can be achieved in one operation. Raising the temperature also speeds up the rate of deuteration.

The reaction speed depends on the particular circumstances involving each definite compound. In general it is found that when the thermodynamic enthalpy difference between the isomers is larger than faster reactions occur. When the enthalpy difference is larger than 3 kilocalories per mole then a very fast reaction in general proceeds. If the ethalpy difference lies between 1 and 3 kilocalories per mole reasonable speeds are easily obtained and the equilibrium lies in favor of the more stable compound. If the enthalphy difference is less than 1 kilocalorie per mole the reactions are generally slow at around room temperature. While there is no upper limit to the temperature for this process, side reactions take place at higher temperatures such as cis-transisomerization and polymerization. The preferred temperatures for this reaction lie in the range between 0° C. and 70° C. and more prefered between 20° C. and 50° C.

General Procedure 1

0.03 mole of beta-pinene is taken in a previously dried 100 ml pressure bottle provided with a magnetic stirrer and a Dewar condenser with an inlet for sulfur dioxide gas. The entire set up is maintained under nitrogen atmosphere. Sulfur dioxide gas from a commercial cylinder is provided by the Matheson Chemical Company and is dried by passing through a molecular sieve and is then condensed into the pressure bottle by the dry ice acetone mixture taken in the Dewar condenser. When 60 ml of sulfur dioxide have been collected in the pressure bottle, the bottle is closed by means of a sample collecting set up. The flask is then warmed to room temperature and contents stirred magnetically until the isomerization is complete. The pressure inside the bottle ranges from 35 to 50 pounds per square inch. Sulfur dioxide is now allowed to escape using a sulfur dioxide escape nozzle and is absorbed by a 50% sodium hydroxide solution or if desired it can be recycled. After all of the sulfur dioxide has escaped the pressure bottle, the bottle cap is removed and 50 ml of methylene chloride is added and the resulting solution is dried with a drying material such as sodium sulfate. The organic solution is filtered and concentrated. The crude isomerized olefin is distilled if necessary. The yields are usually quantitative. In the case of highly volatile olefins, for instance pentene, the escaping sulfur dioxide gas removes most of the olefins. In such an eventuality, the escaping olefins are trapped in a layer of ether placed above the 50% sodium hydroxide solution. The isomerization can take place at temperatures above room temperatures but are then carried out in stainless steel bombs instead of the pressure bottle. Otherwise the set up and working procedures are the same. The product obtained was analyzed by gas chromatography, infrared, UV and nmr spectroscopy to estimate quantitatively the extent of the isomerization and the purity of the isomerized olefin.

General Procedure 2

Deuterization of olefins with deuterium oxide in liquid sulfur dioxide

The procedure is identical to the isomerization procedure described in Example 1. Both the olefin (0.05 mole) and 5 to 10 grams of deuterium oxide are taken in the pressure bottle initially. Then sulfur dioxide is condensed onto the olefin and deuterium oxide. Since deuterium oxide forms a layer separate from liquid sulfur dioxide effective stirring is beneficial for deuterization of the olefin. The separation procedure following is very similar to that one employed in the case of isomerization. However, after the removal of the sulfur dioxide 50 ml of methylene chloride is added and the deuterium oxide/water layer is removed before drying the methylene chloride layer. Deuteration procedures can be employed at temperatures higher than room temperature and are carried out in a stainless steel bomb of suitable capacity. The prefered temperature for the deuteration method lies in the range of 0° to 70° C. and more preferably in the range between 20° and 50° C.

EXAMPLE 1

Continuous isomerization of beta-pinene to alpha-pinene using a neutral alumina column Alumina supplied by the Baker Chemical Company which is neutral and suitable for column chromatography was placed in a glass column of 1.8 cm diameter. 140 ml of methylene chloride was added. A solution made up of 100 ml of methylene chloride and 15 ml of liquid sulfur dioxide by volume was then added to the column and drained out. A Dewar condenser was attached to the column to recondense any sulfur dioxide which might try to escape out. As sulfur dioxide passes through the column, the column warms up due to the exothermic process of absorption. When the column has been completely treated with sulfur dioxide 1.72 grams of beta-pinene was added in 1 lot and it was eluted down the column with a solvent mixture containing methylene chloride and sulfur dioxide in a volume ratio of 100 to 15. Sulfur dioxide-methylene chloride mixtures were made by taking the required amount of methylene chloride in a flask cooled in an ice bath and condensing dry sulfur dioxide into the flask using a Dewar condenser.

A yellow band was observed to move down the column. The yellow fraction was collected in a flask and concentrated to yield alpha-pinene in more than 97% yield and 100% optical purity. 3% limonene was also formed. Only trace amount of beta-pinene were seen. There was no loss in the optical purity of the alpha-pinene formed.

EXAMPLE 2

An alumina column used for continuous conversion (Example 1) of beta to alpha-pinene was treated with 5 ml (3.44 g) of beta-pinene and diluted with 150 ml of methylene chloride. Very little conversion was observed. The same column was treated with 2 ml [1.72 grams] of beta-pinene in a mixture of 100 ml of methylene chloride and 10 ml sulfur dioxide. After 1 to 1½ hours 62.7% conversion of beta-pinene to alpha-pinene was observed.

EXAMPLE 3

Using the same column as in Example 2, 2 ml [1.72 grams equivalent 0.02 mole] of beta-pinene was added with a mixture of 100 ml of methylene chloride and 20 ml of sulfur dioxide. The solvent moved slowly and after 2½ hours beta-pinene was completely converted and no beta-pinene was observed in the eluent. However, a certain amount of limonene was observed accompanying the alpha-pinene.

Limonene, which has two double bonds, seems to move a lot slower than pinene in alumina columns activated with sulfur dioxide. A sulfur dioxide loaded alumina column can be effectively used for separating monoolefins from diolefins.

EXAMPLE 4

Regio specific isomerization of olefins in liquid sulfur dioxide

In Table 1 (appearing at the end of this specification) there is shown a number of olefins each of which was isomerized preponderantly to a single isomeric olefin by the General Procedure 1. The degree of isomerization was observed optically and with nuclear magnetic resonance spectroscopy, infrared spectoscopy and gas chromatography. The relative reaction rate was determined and compared with the enthalpy difference of the isomer pairs.

EXAMPLE 5

A solution of 0.136 grams, 1 millimole of beta-pinene was dissolved in 1 ml sulfur dioxide and was sealed in a nuclear magnetic resonance tube at −78° C. The isomerization to alpha pinene was followed at room temperature by the disappearance of the signal at $\delta=4.54$ and the appearance of a multiplet at $\delta=5.19$. The reaction exhibited a clear pseudo first order characteristic with a rate constant of 3.01 times $10^{-5}$ minute$^{-1}$.

EXAMPLES 6-10

Under similar reaction conditions as in Example 5, methylenecyclohexane, methylenecyclopentane, 2-methyl-1-pentene, 2,4,4-trimethyl-2-pentene and 2,3-diphenyl-1-propene underwent the isomerization to the thermodynamically more stable isomers shown in Table 1. The isomerization of 2-methyl-1-pentene afforded only 2-methyl-2-pentene and 4-methyl-2-pentenes were not observed.

By comparison both cis and trans-4-methyl-2-pentenes appear to be quite stable under the same reaction conditions. Moreover the compound 4-methyl-1-pentene was stable in sulfur dioxide in the dark; and in the presence of light, polymer formation took place.

The comparison of the rates of isomerization with the relative thermodynamic stabilities of olefin pairs as stated in Table 1 and the absence of other possible isomers in the reaction mixtures strongly imply a kinetically controlled process. The rate of isomerization of beta-pinene in sulfur dioxide at 60° C. is increased only by a factor of about 5. If the same reaction takes place in the presence of a catalytic amount of anhydrous aluminum chloride then a mixture of p-menthenes and a small quantity of a polymer form.

EXAMPLE 11

P-Menth-1-ene with a rotation [+82.6°] in sulfur dioxide was racemized at room temperature in 4 hours. This fast racemization provides additional evidence for the 1,3 arrangement of secondary allyl sulfenic acids.

EXAMPLE 12

2,2,6,6-tetradeutero methylene cyclohexane was dissolved in sulfur dioxide and maintained at room temperature for 3 hours, resulting in the formation of 1,2,6,6-tetradeutero-1-methyl cyclohexene. Further reaction for 24 hours resulted in statistical distribution of the 4 deuteriums and 2 hydrogens among the 6 carbon hydrogen bonds on the next nearest neighbor carbon atoms relative to the tertiary carbon atom of the methylene cyclohexane. Under the conditions set forth only exchange took place; isomerization generally requires larger transition energies.

EXAMPLES 13-18

A compound of the formula given on the left side in Table 2 was dissolved in sulfur dioxide containing deuterium oxide at room temperature. Reaction under the conditions indicated in Table 2 lead to a compound having the formula indicated on the right side of Table 2.

The percentage of the deuterium expected to be incorporated together with the observed value is given in the right hand column for Examples 13, 14, 16, 17, 18. For Example 15 the same column gives the change in the angle of the optical rotation.

Since various changes and modifications may be made in the invention without departing from the spirit and essential characteristics thereof it is intended that all matter contained in the above description shall be interpreted as illustrative, only the invention being limited by the scope of the appended claims.

Table I

Regiospecific Isomerization of Olefins in Liquid Sulfur Dioxide[a]

| Example | Olefin (OL) | Isomerized Olefin (IOL) | IOL/OL | Relative Rate[b] | H° (kcal/mol) |
|---|---|---|---|---|---|
| 5 | β-Pinene | α-Pinene | 97/trace[c] | 1 | −2.4[i] |
| 6 | Methylenecyclohexane | 1-Methylcyclohexene | 99/trace | ca 800 | −2.1[ii] |
| 7 | Methylenecyclopentane | 1-Methylcyclopentene | 99/trace | very fast | −3.8[ii] |
| 8 | 2-Methyl-1-pentene | 2-Methyl-2-pentene | 91/9[d] | 630 | −1.46[iii] |
|   | 4-Methyl-2-pentene (cis- and trans) |  | N.R. |  |  |
| 9 | 2,4,4-Trimethyl-2-pentene | 2,2,4-Trimethyl-1-pentene | 81/19[d] | — | −1.3[iv] |
| 10 | 2,3-Diphenyl-1-propene | 2,3-Diphenyl-2-propene | 75/trace[e] | 142 | — |

[a]Reactions were carried out in ca 1M solutions in sulfur dioxide in a sealed NMR tube at room temperature;
[b]The pseudo first order rate constants relative to the value of $3.01 \pm 0.165 \times 10^{-5}$ min$^{-1}$ for the isomerization of beta-pinene. More refined kinetic data will be published in a full paper;
[c]Accompanied with ca 3% p-menthadienes;
[d]The equilibrium approached from both sides;
[e]Both trans-(62%), and cis-(13%)-olefins were formed. In addition about 25% of a polymer was present;
[i]D. V. Banthrope and D. Whittaker, Chem. Rev., 66, 643(1966);
[ii]R. B. Turner, and R. H. Garner, J.Am.Chem.Soc., 80, 1424 (1958).
[iii]"Selective Values of Properties of Hydrocarbons and Related Compounds," American Petroleum Institute - Project 44. April 30, 1975, Table 8p (Part 2);
[iv]R. B. Turner, D. E. Mettleton Jr. and M. Perelman, J.Am.Chem.Soc., 80, 1430(1958).

Table 2

REGIOSPECIFIC HYDROGEN/DEUTERIUM EXCHANGE

| Example |  | % D Incorporated (expected/observed) |
|---|---|---|
| 13 | [methylenecyclohexane] RT/2hr → [1,1-D2-methylenecyclohexane with D2] | 73/73 |
| 14 | [methylcyclohexene] RT/5 days → [cyclohexene with H, D2, CD3] | 75/52 |

Table 2-continued
REGIOSPECIFIC HYDROGEN/DEUTERIUM EXCHANGE

| Example | | % D Incorporated (expected/observed) |
|---|---|---|
| 15 | 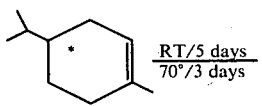 | +82.6° → +79.5° |
| 16 | 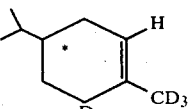 | +50.6°<br>71/67 |
| 17 | 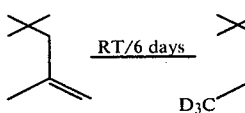 | 67/50 |
| 18 |  | 89/60<br>90/86 |

We claim:

1. A method for deuterating an olefinic compound having a first nucleus of hydrogen or isotope thereof attached to a carbon atom vicinal to a tertiary double bonded carbon atom comprising:
   maintaining said compound in solution in liquid sulfur dioxide and providing the oxide of a hydrogen isotope in the sulfur dioxide solution whereby said first nucleus is exchanged in said compound for a nucleus of a hydrogen isotope present in the sulfur dioxide solution.

2. A method as set forth in claim 1 comprising:
   (a) substituting at the place left uncoordinated by the removal of the first nucleus with a second like nucleus.

3. A method as set forth in claim 2 wherein one of the nuclei is a proton and the other nucleus is a deuterium nucleus.

4. A method as set forth in claim 2 wherein the first nucleus is a deuterium nucleus and wherein the second nucleus is a proton.

5. A method as set forth in claim 1 wherein the compound is 2,2,6,6-tetradeutero methylenecyclohexane.

* * * * *